United States Patent [19]

Chernomorsky

[11] Patent Number: 4,797,392

[45] Date of Patent: Jan. 10, 1989

[54] USE OF ANORECTAL COMPOSITIONS

[76] Inventor: Simon A. Chernomorsky, P.O. Box 2882, Elizabeth, N.J. 07207

[21] Appl. No.: 6,780

[22] Filed: Jan. 27, 1987

[51] Int. Cl.⁴ .................... A61K 31/555; A61K 31/40
[52] U.S. Cl. ...................................... 514/185; 514/410
[58] Field of Search ............................... 514/185, 410

[56] References Cited

U.S. PATENT DOCUMENTS 2,120,667  6/1938  Gruskin .............................. 514/410
2,729,586  1/1956  Peck .................................... 514/410

OTHER PUBLICATIONS

*Handbook of Nonprescription Drugs,* Fifth Edition, pp. 63–69, Amer. Pharm. Assoc., Wash. D.C.

Primary Examiner—Frederick E. Waddell
Attorney, Agent, or Firm—Edward A. Meilman

[57] ABSTRACT

Compositions containing by weight chlorophyllin complex in an amount of between about 0.1% and 40.0%, alone or combined with at least one compound from the group consisting of local anesthetics, vasoconstrictors, protectants, counterirritants, astringents, keratolytics, anticholinergics, wound-healing and antimicrobial (antiseptic) agents and one appropriate base (vehicle) from the group consisting of suppositories, ointments, foams, sprays and medicated pads bases for external and intrarectal applications are used to treat anorectal diseases including hemmorrhoids.

3 Claims, No Drawings

USE OF ANORECTAL COMPOSITIONS

BACKGROUND OF THE INVENTOON

The present invention relates to the treatment of anorectal diseases including hemorrhoids by the application of novel pharmaceutical compositions containing a unique agent possessing wound-healing and antimicrobial properties.

There are currently a number of compositions for treatment of anorectal diseases including hemorrhoids. Some of them are based on anesthetic (U.S. Pat. No. 4,118,480) or vasoconstrictive (U.S. Pat. Nos. 3,608,074; 4,145,441; 4,383,986) properties of active agents and are used only to give temporary symptomatic relief. Others, whose mechanism of activity is unknown, have been limited to external application (U.S. Pat. Nos. 3,950,540; 3,950,541).

In contrast to compositions used for temporary relief, sustained symptomatic relief can be achieved by treating anorectal diseases including hemorrhoids with preparations containing wound-healing agents. Anorectal diseases are often initiated by the breakdown of epithelium, dermis, and other subcutaneous tissues which may result in a variety of wounds including fissures, cracks, abscesses, and hemorrhoids. But even when tissues still remain intact, as it is sometimes the case for certain types of hemorrhoids, they are considered as wounds because inflammation occurs. Inflammation of tissues is associated with many symptoms, including heat, redness, pain, itching and swelling. Wound-healing agents relieve these symptoms and provide long-lasting symptomatic relief by promoting tissue repair, reducing inflammation and encouraging wound healing. Recently, several U.S. Pat. Nos. 4,169,143; 4,192,866; 4,508,728 disclose compositions containing certain healing agents for treatment of hemorrhoids and other anorectal diseases.

It is also known that the presence of microorganisms such as fungi, bacteria, yeast and others delay healing and retard tissue repair. U.S. Pat. No. 4,518,583 discloses the use of compositions containing antimicrobial agents to treat anorectal diseases including hemorrhoids.

However, none of the above-cited treatments have been shown to be completely effective in satisfactory managing the symptoms of anorectal diseases including hemorrhoids, and in some cases the treatments themselves contribute to further problems such as causing allergies or additional tissue irritation.

It has been found that the entity known as chlorophyllin complex is more effective than the foregoing treatments for managing anorectal diseases including hemorrhoids while also lacking some of the undesirable side effects exhibited by some of the other treatments. The advantages of using chlorophyllin complex will be more apparent in the description of the invention which follows.

In the past, chlorophyllin copper complex has been disclosed for use in the treatment of ulcerative lesions, burns, wounds, especially with infected tissues, to promote their healing (U.S. Pat. Nos. 2,120,667; 2,729,586), in a poultry feed to prevent and control of duck disease (U.S. Pat. No. 2,646,384), as a body deodorant (U.S. Pat. No. 2,794,762), to improve alcoholic beverages' odor (Japanese Patent No. 81,106,586), for treatment of feces and urine of pets (Japanese Patent No. 85,120,926), to increase the stability of vitamin C (Japanese Patent No. 7743 ('57)) as a food dye to color gelatin capsules (Japanese Patent No. 80,161,863) and toothpastes (Japanese Patent No. 85,48,918). However, chlorophyllin copper complex is not disclosed in patents or other prior art for treatment of anorectal diseases including hemorrhoids. Chlorophyllin copper complex is safe and approved by the U.S. Food and Drug Administration for internal use as a deodorant (Federal Register, 50, 2516-7, 1985).

SUMMARY OF THE INVENTION

The principal objects of this invention are to provide compositions for use in the anorectal area; to provide such compositions with a unique water-soluble active agent which can be uniformly distributed in the effected region and are easy to apply; to provide such compositions which have long-lasting effects; to provide such compositions which enhance healing of injured tissue; to provide such compositions which reduce inflammation; to provide such compositions which soothe itching and burning; to provide such compositions which reduce irritation and swelling of diseased tissue; to provide such compositions which give relief from pain associated with anorectal diseases including hemorrhoids; to provide such compositions which relieve discomfort; to provide such compositions which inhibit growth and development of microorganisms in the anorectal area; to provide such compositions which inhibit activity of toxins produced by microorganisms in the anorectal area; to provide such compositions which can be used for treatment of lesions other than hemorrhoids (fissures, cracks, fistulas, abscesses) in the anorectal area; and to provide such compositions which have no unfavorable side effects.

To achieve the above-mentioned objects, there are provided pharmaceutical compositions containing as an active agent chlorophyllin complex dissolved or dispersed in an appropriate base (vehicle) which can be suppositories, ointments, foams, sprays and medicated pads.

It can also be beneficial to include in anorectal compositions containing chlorophyllin complex other active agents from different pharmacological groups such as local anesthetics, vasoconstrictors, protectants, counterirritants, astringents, keratolytics and anticholinergics. It may be even rational to include in anorectal compositions containing chlorophyllin complex other wound-healing and antimicrobial agents. In this case, the effectiveness of compositions may be sufficiently enhanced since the woundhealing and antimicrobial properties of, for example, chlorophyllin copper complex and these other agents may be dependent on different mechanisms of activities.

The various aspect of the present invention will be more fully understood upon a reading of the following portions of the specification.

DESCRIPTION OF THE PREFERRED EMBODIMENTS

The improved anorectal compositions used in the present method contain as a main active agent a chlorophyll derivative, such as chlorophyllin or its derivatives, preferably chlorophyllin metal (most preferably copper) complex and the base (vehicle). The chlorophyllin metal complex used in the invention is a water-soluble derivative of chlorophyll, the naturally occurring green pigment. The water-soluble sodium or potassium salts are preferable but the invention should be taken to include other water-soluble derivatives such as those containing ammonium and other basic cationic ions. Also, other chlorophyll derivatives with or without central metal atoms and existing as free acids or combinations therewith such as esters, ethers, amides, and salts or as other chemical modifications of the chlorophyll molecule are embodied in the present invention. Metals other than copper include iron, zinc, cobalt, platinum, silver, gold, and the like metals. The chlorophyll derivative is used in an amount by weight of between about 0.1%–40.0%, and more preferably between about 0.5%–2.0%. The complex is applied topically in an anti-anorectal disease effective amount which can number, for example, up to four 10–40 mg containing suppositories per day. The particular amount is best determined by the attending clinician.

As mentioned earlier, the anorectal compositions may be formulated as suppositories, ointments, foams, sprays and medicated pads.

The suppository compositions may contain either hydrophobic or hydrophilic bases and can include, for example, cocoa butter, glycerinated gelatin, hydrogenated vegetable oils, mixtures of polyethylene glycols of various molecular weights, polyoxyethylene sorbitan fatty acid esters and polyethylene stearates; polyvinyl alcohol, polyvinyl pyrrolidone, polyacrylamide, chemically modified starch or combinations of these materials (U.S. Pat. No. 4,406,883).

The ointment compositions may contain water-miscible bases such as hydrophilic ointment, U.S.P., for example; water-absorbing bases such as lanolin, U.S.P.; and hydrophilic petrolatum, U.S.P., for example; hydrocarbon bases such as white petrolatum, U.S.P., for example; water-soluble bases such as polyethylene glycol ointment, N.F., for example.

The foam and spray bases may contain one or more of the following: propellants, aqueous and nonaqueous solvents, surfactants and suspending agents.

The medicated pad bases may contain one or more of the following: water, glycerin, propylene glycol, alcohol and hamamelis water.

Along with the preferred chlorophyllin copper complex, anorectal compositions of the invention can contain other active agents. They may include such local anesthetics and/or their salts as benzocaine, diperodon, pramoxine, dibucaine, camphor, phenol, tetracaine, and phenacaine, in an amount by weight of between about 0.25% and 25.0%. Anorectal compositions of the invention may also contain ephedrine, phenylephrine and/or their salts as vasoconstrictors in an amount by weight of between about 0.005% and 1.5%. The following protectants as aluminum hydroxide gel, calamine, cocoa butter, cod or shark liver oil, glycerin in aqueous solution, kaolin, lanolin, mineral oil, starch, white petrolatum, wool alcohol, zinc oxide, vegetable or castor oil, polyethylene glycol, propylene glycol can be used in anorectal compositions of this invention in an amount by weight of between 5.0% and 88.0%. Anorectal compositions of the invention can also contain menthol in aqueous solution as a counterirritant in an amount by weight of between about 0.25% and 2.5%. Astringents such as calamine, zinc oxide, hamamelis water, bismuthresorcinol compound, bismuth subgallate, peruvian balsam, aluminum chlorhydroxy allantoinate and tannic acid may be present in anorectal compositions of the invention in an amount by weight of between about 0.2% and 60.0%. Furthermore, the wound-healing agents can be included in anorectal compositions of the invention selected from the group consisting of vitamin A and vitamin D by weight in an amount of between about 0.005% and 0.04%, peruvian balsam by weight in an amount of between about 0.5% and 2.5%, cod liver oil and/or shark liver oil by weight in an amount of between about 1.0% and 6.0%, and live yeast cell derivative in an amount of between about 2–50,000 units/g. Also, antimicrobial (antiseptic) agents such as benzethonium chloride, benzalkonium chloride, boric acid, 8-quinolinol benzoate, secondary amyltricresols, cetylpyridinium chloride, phenol, menthol, chlorothymol, camphor and 8-hydroxyquinoline sulfate may be used in anorectal compositions of the invention in an amount by weight of between abut 0.02% and 40.0%. Anorectal compositions of the invention may contain aluminum chlorhydroxy allantoinate and resorcinol as keratolytics in an amount by weight of between about 0.2% and 3.5%. Finally, atropine or other solanaceous type alkaloids, either alone or in admixture, can be used as anticholinergics in anorectal compositions of the invention in an amount by weight of between about 0.02% and 0.1%.

In the above described compositions for treating anorectal diseases, including hemorrhoids, chlorophyllin copper complex increases tissue oxygen consumption, demonstrates fibroblast growth-stimulating effects and accelerates healing of wounds and ulcers. It imparts to the compositions an ability to affect microbial growth and/or inhibit toxins produced by microorganisms. In addition, the compositions containing chlorophyllin copper complex coat the treated tissue which provides high concentrations of the active agent in the diseased areas. Since chlorophyllin copper complex is permitted by the U.S. Food and Drug Administration for use as an internal deodorant, the compositions containing this compound are very safe. Thus, compositions with chlorophyllin copper complex provide highly useful combinations of properties required for treatment of anorectal diseases, including hemorrhoids.

Compositions have been formulated according to the following examples wherein the ingredients are listed in weight percentage. Because there are no clear differences between ointments, creams, gels, jellies and pastes, any of these terms are implied whenever the term "ointment" is used in the description of this invention.

The below-mentioned formulations are examples of different types of compositions containing chlorophyllin copper complex to treat anorectal diseases, including hemorrhoids. Many other types of formulations of suppository, ointment, foam, spray and medicated pad bases may be used in this invention as well.

| Example of suppositories | |
|---|---|
| #1 | |
| Chlorophyllin copper complex | 1.0% |
| Cocoa butter | 99.0% |
| #2 | |
| Chlorophyllin copper complex | 1.0% |
| Polyethylene glycol base | 99.0% |
| (Polyethylene glycol 400 - 60% | |
| Polyethylene glycol 8000 - 40%) | |
| #3 | |
| Chlorophyllin copper complex | 1.0% |
| Benzocaine | 5.0% |
| Polyethylene glycol base | 94.0% |
| (Polyethylene glycol 400 - 60% | |
| Polyethylene glycol 8000 - 40%) | |

Example of suppositories -continued

4
| | |
|---|---|
| Chlorophyllin copper complex | 1.0% |
| Witepsol WH-15 | 99.0% |

5
| | |
|---|---|
| Chlorophyllin copper complex | 1.0% |
| Water | 9.0% |
| Glycerin | 70.0% |
| Gelatin granular | 20.0% |

6
| | |
|---|---|
| Chlorophyllin copper complex | 1.0% |
| Bismuth subgallate | 2.25% |
| Bismuth-resorcinol compound | 1.75% |
| Benzyl benzoate | 1.2% |
| Peruvian balsam | 1.8% |
| Zinc oxide | 11.0% |
| Hydrogenated vegetable oil | 81.0% |

7
| | |
|---|---|
| Chlorophyllin copper complex | 1.0% |
| Ephedrine sulfate | 0.1% |
| Witepsol WH-15 | 98.9% |

8
| | |
|---|---|
| Chlorophyllin copper complex | 1.0% |
| Menthol | 0.4% |
| Cocoa butter | 98.6% |

9
| | |
|---|---|
| Chlorophyllin copper complex | 1.0% |
| Live yeast cell derivative per suppository | 200 units |
| Whitepsol WH-15 to make | 100.0% |

10
| | |
|---|---|
| Chlorophyllin copper complex | 1.0% |
| Benzalkonium chloride | 0.05% |
| Witepsol WH-15 | 98.95% |

11
| | |
|---|---|
| Chlorophyllin copper complex | 1.0% |
| Atropine | 0.05% |
| Witepsol WH-15 | 98.95% |

Example of Ointments

1
| | |
|---|---|
| Chlorophyllin copper complex | 2.0% |
| Hydrophilic Ointment, U.S.P. | 98.0% |

2
| | |
|---|---|
| Chlorophyllin copper complex | 2.0% |
| Hydrophilic Petrolatum, U.S.P. | 98.0% |

3
| | |
|---|---|
| Chlorophyllin copper complex | 2.0% |
| White Petrolatum, U.S.P. | 98.0% |

4
| | |
|---|---|
| Chlorophyllin copper complex | 2.0% |
| Pramoxine hydrochloride | 1.0% |
| White Petrolatum, U.S.P. | 97.0% |

5
| | |
|---|---|
| Chlorophyllin copper complex | 2.0% |
| Ephedrine sulfate | 0.1% |
| White Petrolatum, U.S.P. | 97.9% |

6
| | |
|---|---|
| Chlorophyllin copper complex | 2.0% |
| Menthol | 0.2% |
| Hydrophilic Ointment, U.S.P. | 97.8% |

7
| | |
|---|---|
| Chlorophyllin copper complex | 2.0% |
| Zinc oxide | 2.0% |
| White Petrolatum, U.S.P. | 96.0% |

8
| | |
|---|---|
| Chlorophyllin copper complex | 2.0% |
| Live yeast cell derivative per oz. | 2000 units |
| White Petrolatum, U.S.P. to make | 100.0% |

9
| | |
|---|---|
| Chlorophyllin copper complex | 2.0% |
| Benzalkonium chloride | 0.1% |
| White Petrolatum, U.S.P. | 97.9% |

10
| | |
|---|---|
| Chlorophyllin copper complex | 2.0% |
| Allantoin | 0.5% |
| White Petrolatum, U.S.P. | 97.5% |

11
| | |
|---|---|
| Chlorophyllin copper complex | 2.0% |
| Atropine | 0.1% |
| White Petrolatum, U.S.P. | 97.9% |

12
| | |
|---|---|
| Chlorophyllin copper complex | 2.0% |
| Polyethylene Glycol Ointment, N.F. | 98.0% |

Example of Foams & Sprays

1
| | |
|---|---|
| Chlorophyllin copper complex | 2.0% |
| Oil-waxes surfactant | 3.0% |
| Water | 70.0% |
| Propellant 12/114 (60:40) | 25.0% |

2
| | |
|---|---|
| Chlorophyllin copper complex | 2.0% |
| Glycol | 84.0% |
| Emulsifying agent | 4.0% |
| Propellant 12/114 (40:60) | 10.0% |

3
| | |
|---|---|
| Chlorophyllin copper complex | 2.0% |
| Ethyl alcohol | 44.0% |
| Surfactant | 5.0% |
| Water | 34.0% |
| Propellant | 15.0% |

4
| | |
|---|---|
| Chlorophyllin copper complex | 2.0% |
| Pramoxine hydrochloride | 1.0% |
| Ethyl alcohol | 44.0% |
| Surfactant | 5.0% |
| Water | 33.0% |
| Propellant | 15.0% |

5
| | |
|---|---|
| Chlorophyllin copper complex | 2.0% |
| Benzalkonium chloride | 0.1% |
| Ethyl alcohol | 44.0% |
| Surfactant | 5.0% |
| Water | 33.9% |
| Propellant | 15.0% |

6
| | |
|---|---|
| Chlorophyllin copper complex | 2.0% |
| Allantoin | 0.3% |
| Ethyl alcohol | 44.0% |
| Surfactant | 5.0% |
| Water | 33.7% |
| Propellant | 15.0% |

7
| | |
|---|---|
| Chlorophyllin copper complex | 2.0% |
| Hamamelis water | 35.0% |
| Ethyl alcohol | 28.0% |
| Surfactant | 3.0% |
| Water | 22.0% |
| Propellant | 10% |

Example of Medicated Pads
(preparation of the solutions)

1
| | |
|---|---|
| Chlorophyllin copper complex | 2.0% |
| Hamamelis water | 50.0% |
| Glycerin or Propylene glycol | 10.0% |
| Water to make | 100.0% |

2
| | |
|---|---|
| Chlorophyllin copper complex | 2.0% |
| Hamamelis water | 50.0% |
| Glycerin or Propylene glycol | 10.0% |
| Methylparaben | 0.1% |
| Benzalkonium chloride | 0.003% |
| Water to make | 100.0% |

These solutions can be used to impregnate suitable flannel-like materials in order to prepare medicated pads.

While preferred embodiments of the present invention have been disclosed, it will be appreciated that it is not limited thereto, but be otherwise embodied within the scope of the following claims.

What is claimed is:

1. A method of treating hemorrhoids and anorectal fissures, cracks, fistulas and abcesses, which comprises topically applying an anti-anorectal disease effective amount of a chlorophyll derivative to a host in need thereof.

2. The method of claim 1, wherein said derivative is applied in combination with a pharmaceutically acceptable vehicle and said derivative is between 0.1% and 40% of said combination.

3. The method of claim 2, wherein said derivative is chlorophyllin metal complex.

* * * * *